(12) United States Patent
Adriaens et al.

(10) Patent No.: US 7,709,619 B2
(45) Date of Patent: May 4, 2010

(54) DNAZYMES AND SENSORS INCORPORATING THE SAME

(75) Inventors: Peter Adriaens, Brighton, MI (US); Raveender Vannela, Ann Arbor, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 50 days.

(21) Appl. No.: 11/846,796

(22) Filed: Aug. 29, 2007

(65) Prior Publication Data

US 2008/0113359 A1 May 15, 2008

Related U.S. Application Data

(60) Provisional application No. 60/840,994, filed on Aug. 30, 2006.

(51) Int. Cl.
*C07H 21/00* (2006.01)
*C12Q 1/68* (2006.01)
(52) U.S. Cl. .......................................... 536/23.1; 435/6
(58) Field of Classification Search .................. None
See application file for complete search history.

(56) References Cited

U.S. PATENT DOCUMENTS 6,706,474 B1 3/2004 Lu et al.
7,192,708 B2 3/2007 Lu et al.

OTHER PUBLICATIONS

Dahm, S.C. and Uhlenbeck, O.C., Role of divalent metal ions in the hammerhead RNA cleavage reaction. *Biochemistry*, 30, 9464-9469, 1991.
Famulok, M., et al., Nucleic acid aptamers—from selection in vitro to applications in vivo, *Acc. Chem. Res.*, 33, 591-599, 2000.
Faulhammer, D. and Famulok, M., Characterization and divalent metal-ion dependence of in vitro selected deoxyribozymes which cleave DNA/RNA chimeric oligonucleotides. *J. Mol. Biol.*, 269, 188-202, 1997.
Faulhammer, D. and Famulok, M., The $Ca^{2+}$ ion as a cofactor for a novel RNA-cleaving deoxyribozyme, *Angew. Chem. Int. Ed. Engl.*, 35, No. 23/24, 2837-2841, 1996.
Hermann, T. and Patel, D.J., Adaptive Recognition by Nucleic Acid Aptamers. *Science*, 287, 820-825, 2000.
Hesselberth, J., et al., In vitro selection of nucleic acids for diagnostic applications, *Revs. in Mol. Biotechnol.*, 74, 15-25, 2000.
Heyduk, T. and Heyduk, E., Molecular beacons for detecting DNA binding proteins, *Nat. Biotechnol.*, 20, 171-176, 2002.
Jayasena, S.D., Aptamers: an emerging class of molecules that rival antibodies in diagnostics, *Clin. Chem.*, 45:9, 1628-1650, 1999.
Kawakami, J., et al., In vitro selection of aptamers that act with $Zn^{2+}$. *J. Inorg. Biochem.*, 82, 197-206, 2000.
Liu, J. and Lu, Y, A colorimetric lead biosensor using DNAzyme-directed assembly of gold nanoparticles. *J. Am. Chem. Soc.*, 125, 6642-6643, 2003.
Lu, Y., et al., New highly sensitive and selective catalytic DNA biosensors for metal ions. *Biosens. & Bioelecton.*, 18, 529-540, 2003.
Nolan, E.M. and Lippard, S.J., A"Turn-on" fluorescent sensor for the selective detection of mercuric ion in aqueous media. *J. Am. Chem. Soc.*, 125, 14270-14271, 2003.
Santoro, S.W., and Joyce, G.F., A general-purpose RNA-cleaving DNA enzyme. *Proc. Natl. Acad. Sci. USA*, 94, 4262-4266, 1997.
Santoro, S.W. and Joyce, G.F., Mechanism and utility of an RNA-cleaving DNA enzyme. *Biochemistry.*, 37, 13330-13342, 1998.
Santoro, S. W., et al., RNA cleavage by a DNA enzyme with extended chemical functionality, *J. Am. Chem. Soc.*, 122, 2433-2439, 2000.
Schlosser, K., et al., Characterization of long RNA-cleaving deoxyribozymes with short catalytic cores: the effect of excess sequence elements on the outcome of in vitro selection, *Nucleic Acids Res.*, V. 34, #8, 2445-2454, 2006.
Silverman, S., In vitro selection, characterization, and application of deoxyribozymes that cleave RNA. *Nucleic Acids Res.*, V. 33, #19, 6151-6163, 2005.
Thomas, J.M., et al., High affinity DNAzyme-based ligands for transition metal cations—a prototype sensor for $Hg^{2+}$. *Org. Biomol. Chem.*, 2, 307-312, 2004.
Zivarts, M., Liu, Y. and Breaker, R.R., Engineered allosteric ribozymes that respond to specific divalent metal ions. *Nucleic Acids Res.*, V. 33, #2, 622-631, 2005.

*Primary Examiner*—Richard Schnizer
*Assistant Examiner*—Jennifer Pitrak
(74) *Attorney, Agent, or Firm*—Dierker & Associates, P.C.

(57) ABSTRACT

An arsenic ion active DNAzyme includes a nucleotide sequence, which has a base sequence selected from ATCTCCTCCTGTTC (SEQ ID NO: 62), ATCTGCTCCTGTTC (SEQ ID NO: 63), ATCTCCTCATGTTC (SEQ ID NO: 64), ATCTCCTCTTGTTC (SEQ ID NO: 65), ATCTCCAACCTGTTC (SEQ ID NO: 66), and CCGTAGCGCAAAT (SEQ ID NO: 67). A mercury ion active DNAzyme includes a nucleotide sequence, which has a base sequence selected from AATTCCGTAGGTCCAGTG (SEQ ID NO: 68), AATTCGTCGGTCCAGTG (SEQ ID NO: 69), AATTCCGCCGGTCCAGTG (SEQ ID NO: 70), GGTTCCGAGTCTCGCGTG (SEQ ID NO: 71), and CGTTCAAAAGGGGCACTG (SEQ ID NO: 72). Sensors incorporating the respective DNAzymes are also disclosed.

11 Claims, 7 Drawing Sheets

Pool-A

Acceptor(Y;18-nt)    Library-(X; 72-nt)
GGTCTGTCCFArQTGTCGA    pTCCGTAAAG-$N_{45}$-GCACGACGAGGTTTACAC
CCAGACAGGAT-AACAGCT --- AGGCATTTCG
Template T Primer 1: GTGTAAACCTCGTCGTGC
Primer 2: GGTCTGTCCAT-ATGTCGA--TCCGTAAAG
Primer 3: GGTCTGTCCAT-ATGTCGAr

Pool-B

Acceptor (Y;18-nt)    Library-(X; 62-nt)
GGTCTGTCCFArQTGTCGA    pTCCGTAAAG-$N_{35}$-GCACGACGAGGTTTACAC
CCAGACAGGAT-AACAGCT --- AGGCATTTCG
Template T Primer 1: GTGTAAACCTCGTCGTGC
Primer 2: GGTCTGTCCAT-ATGTCGA-TCCGTAAAG
Primer 3: GGTCTGTCCAT-ATGTCGAr

Figure 1

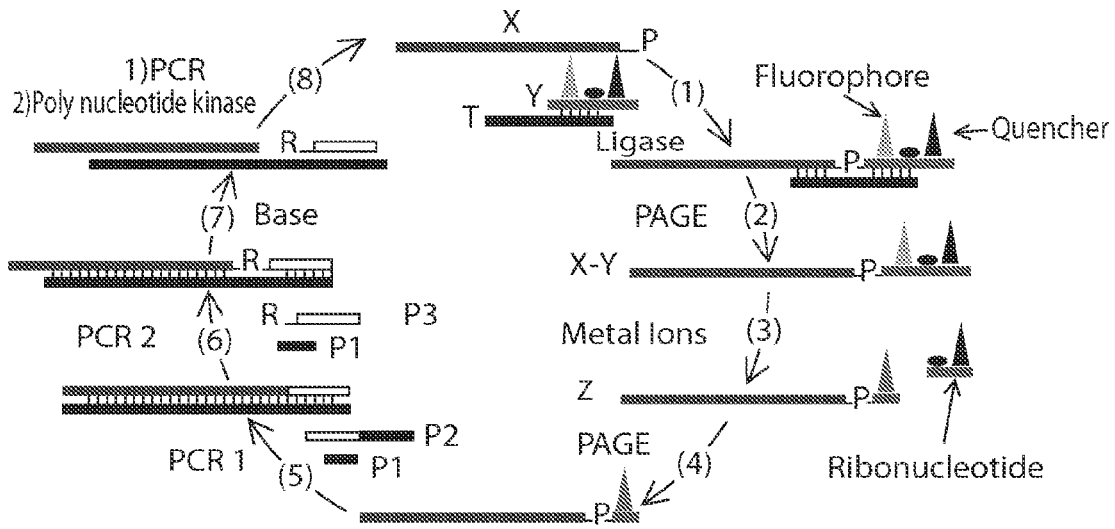

FIGURE 2

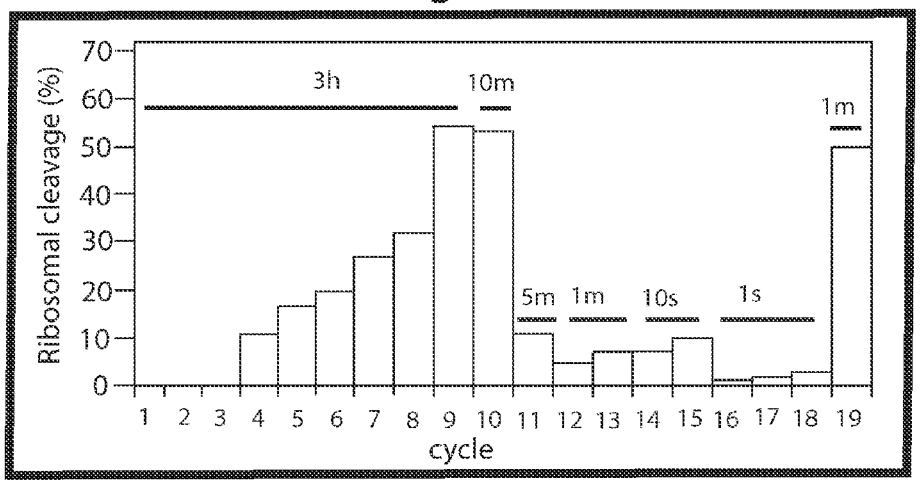

Figure 3

Family-Im
*Mer-1* GGACCTACGGTTCAGTAATTCCGTAGGTCCAGTGCCGCTTACGT
*Mer-2* AGGATTGGGGTCAGTAATTCCGTAGGTCCAGTGACGCTTACTA
*Mer-3* ATTGTTACCGTACAGTAATTCCGTCGGTCCAGTGCCGCTTACGC
*Mer-5* ACACTTGCCGTAACGTAATTCCGTAGGTCCAGTGCCGCGGACA
*Mer-8* ACGCTTATTGTCACGTAATTCCGTAGGTCCAGTGGCGCTTACGG
*Mer-9* AAGCTTACAATCTCGTAATTCCGTAGGTCCAGTGCCGCTTACGC
*Mer-10* AGGCTTACCCTCCCTAATTCCGTAGGTCCAGTGCCGCTTACGT
*Mer-13* AGCCTGACCTTCCCGAATTCCGTAGGTCCAGTGACGAGTACGT
*Mer-14* AATTTTACCGTCCCGAATTCCGTAGGTCCAGTGCCGCTTACGT
*Mer-15* ACTTACCGTAGGGTGAATTCCGTAGGTCCAGTGCCGCTTACGT
*Mer-16* AGGCTTACCGTCCCGTAATTCCGTAGGTCCAGTGCCGCTTACGT
*Mer-19* AATCTTACCGTTACGTAATTCCGTAGGTCCAGTGCGGCCTTACG
*Mer-24* ATGCTTACGCTAGCGTAATTCCGTAGGTCCAGTGCCGCTTGCGT
*Mer-25* ACGCTTACCGTCCCGTAATTCCGCCGGTCCAGTGCAAGCTTACC
*Mer-26* ATCCTTACCGTCCCGTAATTCCGTAGGTCCAGTGCAGCTTATGA
*Mer-27* ACTCTTACAATCCCGTAATTCCGTAGGTCCAGTGCGGCTTAAGT

Figure 4A

Family-IIm
*Mer-4* AGGCTTACCGTCCCGTGGTTCCGAGTCTCGCGTGACGCTTACGT
*Mer-6* AAACTTACCCTCACGTGGTTCCGAGTCTCGCGTGACGCTTACGT
*Mer-7* AGGCTTACTTTCTCGTGGTTCCGAGTCTCGCGTGCCGCTTACGT
*Mer-11* ATTCGGACCGTCGGTGGTTCCGAGTCTCGCGTGCCCGTATACGT
*Mer-12* ACGCTCACCGTCCCGGGTTCCGAGTCTCGCGTGCCGCTTACGTC
*Mer-17* ATGCATATCGACCGTGGTTCCGAGTCTCGCGTGCCGCTTACGTC
*Mer-23* ACGCTTACAATTAGCCGGTTCCGAGTCTCGCGTGCAACTTAAGT

Figure 4C

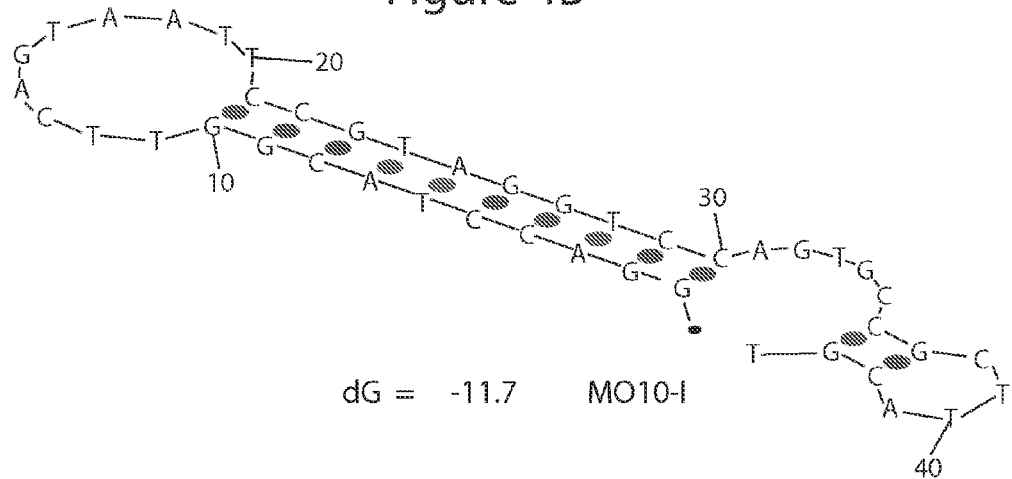
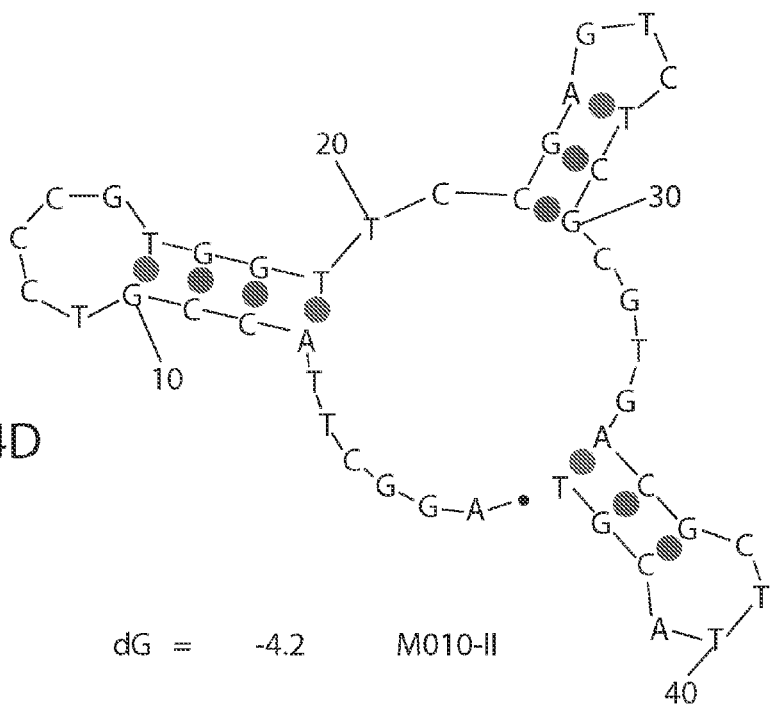

Family-IIIm
*Mer-18* AGGCTTATCGTGGCGCGTTCAAAAGGGGCACTGCCGCTTACGT
*Mer-20* ATTCTTAGCGTACGTCGTTCAAAAGGGGCACTGCCGCTTACGT
*Mer-21* ACGCTTAACGTCCAACGTTCAAAAGGGGCACTGCCAATTACGT
*Mer-22* ATGCTTACCGTCCTTTCGTTCAAAAGGGGCACTGCCGCTTACG dG = -5.7   M010-III

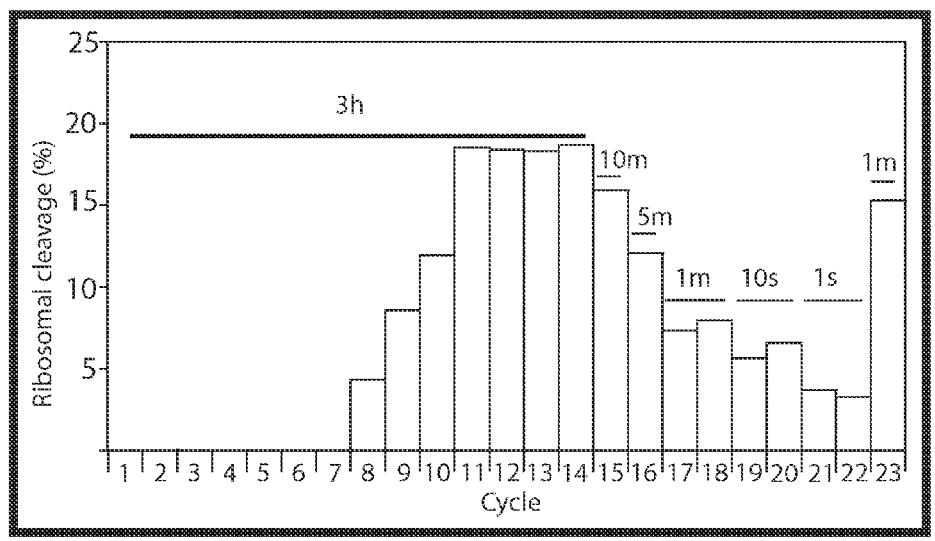

Figure 5

Family-Ia
*Ars-3* GGACCTACGGTTCAGTATCTCCTCCTGTTCGGTTGCCGCTTACG
*Ars-5* AGCATTGGGGTCAGTATCTCCTCCTGTTCCGGACGCTTACTA
*Ars-6* GCGTCAACCGTACAGTATCTGCTCCTGTTCGAGAACCGCTTACG
*Ars-7* ACACTTGCCGTAACGTATCTCCTCATGTTCATCGCCGCGGACAT
*Ars-8* ACGCTAGTTGTCACGTATCTCCTCCTGTTCAGCCTTACGGGAAT
*Ars-9* AAGCCGGCAATCTCGTATCTCCTCTTGTTCCAAGCTTACGCCCA
*Ars-11* ATTCTTACCCTCCCTATCTCCTCCTGTTCTAGTGCCGCTTACGT
*Ars-13* ACCCTGACCTTCCCGATCTCCTCCTGTTCAGTGACGAGTACGTA
*Ars-14* AGTTTTACCGTCCCGATCTCCTCCTGTTCGGTGCCGCTTACGTA
*Ars-15* AATATACCGTAGGTGATCTCCAACCTGTTCTGTGCCGCTTACC
*Ars-16* ACTCCTTACCGCCCGTATCTCCTCCTGTTCCAGTGCCACTTAGT
*Ars-17* AATGGATACGTTACGTATCTCCTCCTGTTCAGTGCGGCCTTAGT

Figure 6A

Family-IIa
*Ars-1* CGACCTACGGTTCAGTCCGTAGCGCAAATTCAGTGTTCGGCTTCG
*Ars-2* CGGATTGGCCTCAGTCCGTAGCGCAAATAGTGACGCTTACTAGG
*Ars-4* ATAATTACCGGTACAGTCCGTAGCGCAAATCACCGGCCGCTTACG
*Ars-10* ACACTTGCAGTAACGTCCGTAGCGCAAATCAGTGAAGCGGACA
*Ars-12* AAGCTTATTGTCACGTCCGTAGCGCAAATTGGTTAATACGGATT

Figure 6C

DNAZYMES AND SENSORS INCORPORATING THE SAME

CROSS-REFERENCE TO RELATED APPLICATIONS

The present application claims the benefit of provisional application Ser. No. 60/840,994, filed Aug. 30, 2006, which is incorporated by reference herein in its entirety.

BACKGROUND

The present disclosure relates generally to DNAzymes, and more particularly to sensors incorporating the DNAzymes.

Many metals pose a risk as environmental contaminants. Some methods for metal analysis, such as atomic absorption spectrometry, inductively coupled plasma mass spectrometry, and anodic stripping voltammetry, often involve sophisticated equipment and sample pre-treatment.

DNAzymes (i.e., DNA enzymes or deoxyribozymes) have been isolated through in vitro selection (Selective Evolution of Ligands through EXponential Enrichment-SELEX) protocols (Sen and Geyer, 1998; Joyce, 2004; Fiammengo and Jaschke, 2005). A variety of deoxyribozymes have been isolated in vitro that are capable of catalyzing different chemical reactions, including RNA or DNA ligation (Carmi et al., 1998; Cruz et al., 2004), phosphorylation (Li and Breaker, 1999), cleavage of phosphoramidate bonds (Burmiester et al., 1997) porphyrin metallation (Li and Sen, 1996) and DNA or RNA cleavage (Carmi et al., 1996; Ting et al., 2004). DNAzymes generally have high stability against chemical and nuclease degradations. This, in combination with the catalytic activity and substrate recognition ability, makes RNA-cleaving DNAzymes potential reagents for biochemical, environmental and pharmaceutical applications.

Biomolecular recognition tools (such as DNAzyme-based ligands (catalytic DNA)) have been developed in recent years. Such tools have the potential to be highly selective and rapid sensors for the detection of transition metal ions. The focus of such tools has been on divalent metal cations. The ligands that emerge from in vitro selections generally range from 20 to 50 nucleotides in length. Due, at least in part, to their high specificity and high catalytic rates (generally below 1.0 $min^{-1}$), these sensors are capable of rapidly screening large numbers of samples. Development of target protocols for geochemically diverse conditions and means for attachment to matrices for relatively simple field deployment may be desirable for rendering such sensors useful to practitioners.

SUMMARY

An arsenic ion active DNAzyme includes a nucleotide sequence, which has a base sequence selected from ATCTC-CTCCTGTTC (SEQ ID NO: 62), ATCTGCTCCTGTTC (SEQ ID NO: 63), ATCTCCTCATGTTC (SEQ ID NO: 64), ATCTCCTCTTGTTC (SEQ ID NO: 65), ATCTCCAACCT-GTTC (SEQ ID NO: 66), and CCGTAGCGCAAAT (SEQ ID NO: 67). A mercury ion active DNAzyme includes a nucleotide sequence, which has a base sequence selected from AATTCCGTAGGTCCAGTG (SEQ ID NO: 68), AATTC-CGTCGGTCCAGTG (SEQ ID NO: 69), AATTCCGCCG-GTCCAGTG (SEQ ID NO: 70), GGTTC-CGAGTCTCGCGTG (SEQ ID NO: 71), and CGTTCAAAAGGGGCACTG (SEQ ID NO: 72). Sensors incorporating the respective DNAzymes are also disclosed.

BRIEF DESCRIPTION OF THE DRAWINGS

Objects, features and advantages of embodiments of the present disclosure will become apparent by reference to the following detailed description and drawings, in which:

FIG. 1 depicts DNA sequences of Pool-A and Pool-B having library (X) (SEQ ID NOS: 2, 8), acceptor (Y) (SEQ ID NOS: 1, 7), and template (T) (SEQ ID NOS: 3, 9), and the primers (SEQ ID NOS: 4-6, 10-12) used in the in vitro selection protocol;

FIG. 2 is a schematic view of the selection scheme of catalytic DNAzymes;

FIG. 3 is a graph depicting the selection progress of autocatalytic DNA (Pool-A) with various metal ions in terms of percent cleavage, the DNA molecules that underwent ribosomal cleavage reaction were plotted as a percent fraction of total DNA, the original DNA concentration was 500 pmoles at 100 nM, the cleavage reactions were quenched by the addition of 10 µl of 25 mM EDTA (pH 8.0), and samples were then resolved by 10% denaturing polyacrylamide gel electrophoresis (PAGE);

FIGS. 4A and 4B depict a first family of mercury active sequences (SEQ ID NOS: 13-28) that were isolated after the $19^{th}$ cycle of in vitro selection, and a representative secondary structure (SEQ ID NO: 29) of the family predicted by M-fold software, respectively;

FIGS. 4C and 4D depict a second family of mercury active sequences (SEQ ID NOS: 30-36) that were isolated after the $19^{th}$ cycle of in vitro selection, and a representative secondary structure (SEQ ID NO: 37) of the family predicted by M-fold software, respectively;

FIG. 5 is a graph depicting the selection progress of autocatalytic DNA (Pool-B) with various metal ions in terms of percent cleavage, DNA molecules that underwent ribosomal cleavage reaction were plotted as a percent fraction of total DNA, the original DNA concentration was 500 pmoles at 100 nM, the cleavage reactions were quenched by the addition of 10 µl of 25 mM EDTA (pH 8.0), and samples were then resolved by 10% denaturing PAGE;

FIGS. 6A and 6B depict a first family of arsenic active sequences (SEQ ID NOS: 43-54) that were isolated after the $23^{rd}$ cycle of in vitro selection, and a representative secondary structure (SEQ ID NO: 55) of the family predicted by M-fold software, respectively;

FIGS. 6C and 6D depict a second family of arsenic active sequences (SEQ ID NOS: 56-60) that were isolated after the $23^{rd}$ cycle of in vitro selection, and a representative secondary structure (SEQ ID NO: 61) of the family predicted by M-fold software, respectively;

DETAILED DESCRIPTION

Embodiments of the DNAzymes disclosed herein are catalytically active towards mercury and arsenic, respectively. The enzymes may advantageously be incorporated into sensors that are suitable for detecting the respective ions in various samples. It is believed that the methodology disclosed herein may also lead to DNAzyme nanosensors for other redox-active and non-redox-active metals, such as, for example, uranium, cadmium, copper, chromium, and lead. Without being bound to any theory, it is believed that one can predict the DNA sequence(s) that will be highly selective for the respective ions using the methods discussed herein.

Figures 4E, 4F:
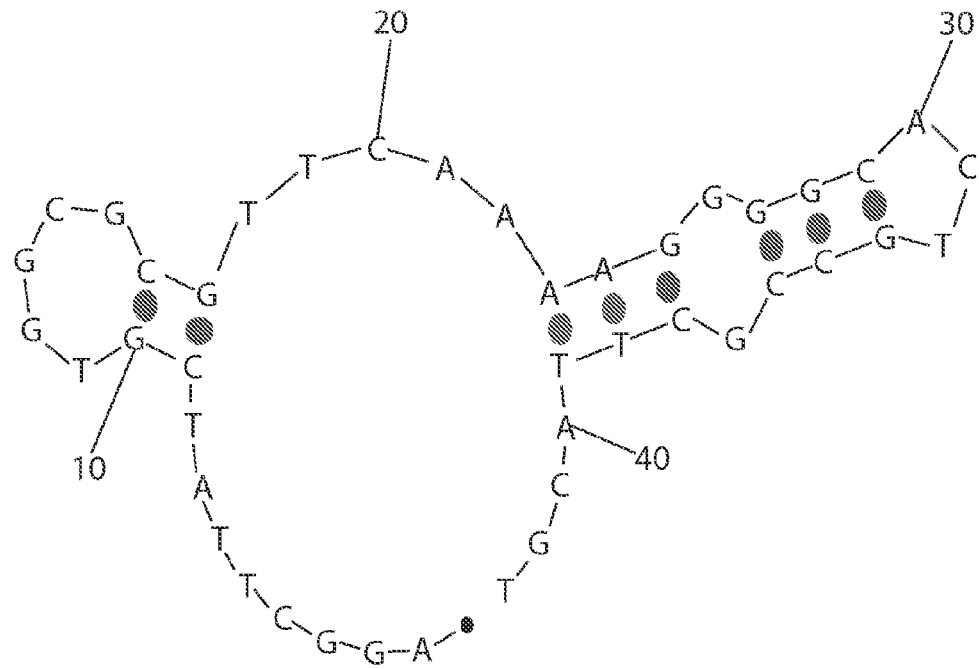
FIGS. 4E and 4F depict a third family of mercury active sequences (SEQ ID NOS: 38-41) that were isolated after the $19^{th}$ cycle of in vitro selection, and a representative secondary structure (SEQ ID NO: 42) of the family predicted by M-fold software, respectively.
Figure 6B:
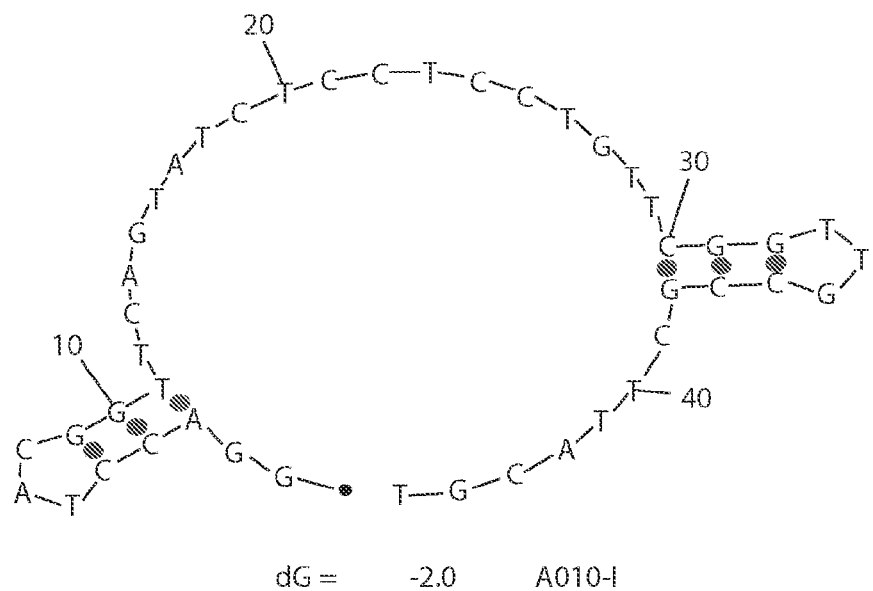
Figure 6D:
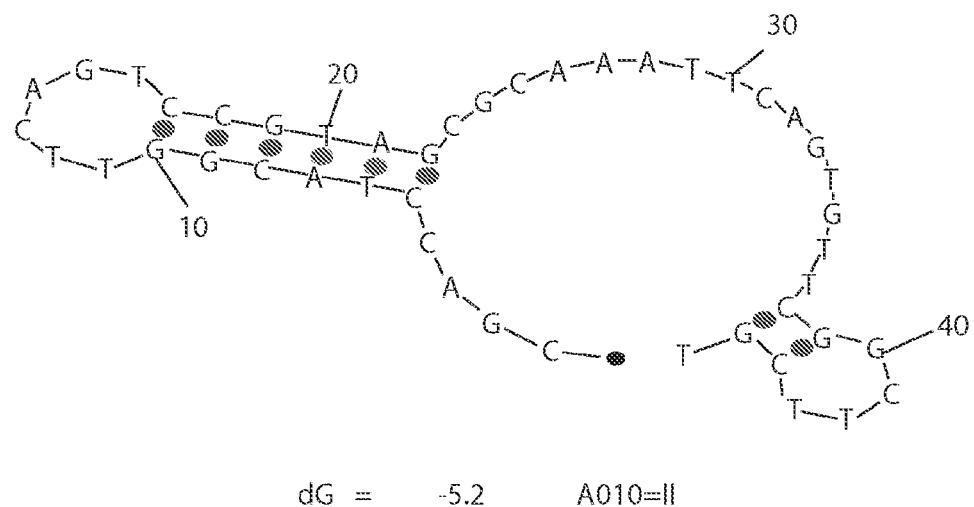

An embodiment of the arsenic ion active DNAzyme disclosed herein has a nucleotide sequence, which includes a base sequence selected from ATCTCCTCCTGTTC (SEQ ID NO: 62), ATCTGCTCCTGTTC (SEQ ID NO: 63), ATCTCTCATGTTC (SEQ ID NO: 64), ATCTCCTCTTGTTC (SEQ ID NO: 65), ATCTCCAACCTGTTC (SEQ ID NO: 66), and CCGTAGCGCAAAT (SEQ ID NO: 67) (examples of which are shown in FIGS. 6A and 6C). An embodiment of the mercury ion active DNAzyme disclosed herein has a nucleotide sequence, which includes a base sequence selected from AATTCCGTAGGTCCAGTG (SEQ ID NO: 68), AATTCCGTCGGTCCAGTG (SEQ ID NO: 69), AATTCCGCCGGTCCAGTG (SEQ ID NO: 70), GGTTCCGAGTCTCGCGTG (SEQ ID NO: 71), and CGTTCAAAAGGGGCACTG (SEQ ID NO: 72) (examples of which are shown in FIGS. 4A, 4C and 4E).

The DNAzymes disclosed herein may advantageously include a single strand of DNA, which is attached to a fluorophore and a quencher of the fluorophore. The fluorophore and quencher are separated by a ribonucleotide. In an embodiment, the fluorophore is attached to the DNA strand at the 3' or 5' end, and then the ribonucleotide is attached to the fluorophore, and the quencher is attached to the ribonucleotide. It is believed that this structure results in less autofluorescence (i.e., background noise) than a double stranded structure, where one of the strands contains the fluorophore and the other of the strands contains the quencher. Furthermore, it is believed that the single stranded structure disclosed herein is more sensitive than a double stranded structure.

The DNAzymes disclosed herein may be isolated via an in vitro selection process. In vitro selection is a technique for isolating RNA or DNA molecules with specific functions from a large number of sequence variants through multiple cycles of selection and amplification (Joyce, 1994; Chapman et al., 1994). In vitro selection has been used to obtain ribozymes with maximized activities or novel catalytic abilities, and to identify oligonucleotides (i.e., aptamers) that bind to certain proteins or small molecules with high affinity. Oligonucleotide/aptamer selection is sometimes referred to as systematic evolution of ligands by exponential enrichment (SELEX) (Tuerk & Gold, 1990).

The in vitro selection process used herein is initiated with a large pool of randomized-sequence nucleotides. Generally, the DNA or RNA library for selection contains $10^{13}$ to $10^{16}$ sequence variants. Chemical synthesis of a set of degenerated oligonucleotides using standard phosphoramidite chemistry allows a completely randomized pool to be constructed. The 3'-phosphoramidite compounds of the A, C, G, and T nucleosides are premixed before being supplied to an automated DNA synthesizer to produce the oligonucleotides. Controlling the ratio of the four phosphoroamidites allow for the identity at each nucleotide position to be completely random (i.e., with equal chance for each base) or biased toward a single base. Other strategies for creating a randomized DNA library include applying mutagenic polymerase chain reaction (PCR) and template-directed mutagenesis (Tsang and Joyce, 1996; Cadwell and Joyce, 1992, 1994).

DNA and RNA molecules may possess both genotype (coding information) and phenotype (encoded function). In vitro selection takes advantage of this unique property. The DNA or RNA molecules in the randomized library are screened simultaneously, and the sequences that exhibit a desired function (phenotype) are separated from the inactive sequences. Such separation may be performed through affinity column chromatography, being linked to or released from a solid support, gel electrophoresis separation, or selective amplification of a tagged reaction intermediate.

The genotype of the active sequences are then copied and amplified, normally through polymerase chain reaction (PCR) for DNA or isothermal amplification reaction for RNA (Guatelli et al., 1990). Mutations can be performed with mutagenic PCR to reintroduce diversity to the evolving system. The selection, amplification and mutation steps are repeated, often with increasing selection stringency, until sequences with the desired activity dominate the pool.

FIG. 2 depicts the general selection cycle used to isolate the mercury and arsenic DNAzymes described herein. The single stranded DNA (X) represents the randomly-sequenced DNA. The sequence is ligated to acceptor DNA Y, which is attached to a template T. The ligated DNA (X-Y) is isolated by polyacrylamide gel electrophoresis (PAGE), thereby removing the template. The purified DNA (X-Y) is incubated with metal ions to cleave the strand at the ribonucleotide (illustrated as the black circle between the fluorophore and the quencher). The cleavage fragment (Z) is then isolated by PAGE.

The recovered DNA is amplified by polymerase chain reaction (PCR) using primers P1, P2. This PCR product is re-amplified using primers P1, P3 to introduce a ribonucleotide linkage within the twice amplified DNA. The resulting double-stranded DNA is treated with NaOH to cleave the RNA linkage. This cleavage fragment is purified by PAGE, phosphorylated at the 5'-end, and used to initiate the next round as a single stranded DNA sequence.

Nucleic acid enzymes developed for a specific metal ion by in vitro selection may have activity in the presence of other metal ions. For example, Mer-27 (SEQ ID NO: 28) (shown in FIG. 4A) is highly selective towards mercury, but is also selective towards copper and zinc. Similarly, Ars-17 (SEQ ID NO: 54) (shown in FIG. 6A) is selective towards arsenic ($As^{5+}$), but is also selective towards cadmium and mercury.

In order to produce nucleic acid enzymes with greater selectivity, a negative selection step may be included in the selection process. As an example, $As^{5+}$-specific deoxyribozymes may be isolated using a selection scheme described in the Examples hereinbelow. In order to obtain deoxyribozymes with high specificity for $As^{5+}$, negative-selections may be carried out in addition to the positive selections in the presence of $As^{5+}$.

For negative selection, the DNA pool is selected against various metal ions. Those sequences that undergo self-cleavage in the presence of metal ions other than $As^{5+}$ are washed off the column. The remaining sequences are further selected with $As^{5+}$ as the cofactor. $As^{5+}$-dependent deoxyribozymes with different affinities for $As^{5+}$ may be obtained by controlling the reaction stringency (i.e., $As^{5+}$ concentration).

As previously stated, the DNAzymes disclosed herein have fluorophores and quenchers attached thereto. The fluorophore is used to measure enzymatic activity and, thus, detect the presence of a particular ion. Any suitable fluorophore may be used, including fluoroscein (e.g., fluoroscein-dT), fluoroscein substitutes, long wavelength dyes, and UV-excited fluorophores.

The quencher molecules absorb the energy of the excited fluorophores. The relatively close proximity of fluorophore and quencher allow for the energy to be transferred from the fluorophore to the quencher. By absorbing this energy, the quencher substantially prevents the fluorophore from releasing the energy in the form of a photon.

Quenchers are either non-fluorescent or fluorescent. Generally, non-fluorescent quenchers are capable of quenching the fluorescence of a wide variety of fluorophores, by absorbing energy from the fluorophore and releasing the energy as heat. Examples of non-fluorescent quenchers include, but are not limited to DABCYL, QSY-7, and QSY-33. Fluorescent quenchers are specific to fluorophores that emit at a specific wavelength range.

Generally, in the presence of the metal ions, the enzyme carries out a catalytic reaction at the ribonucleotide, resulting in cleavage of the ribonucleotide linkage. As a result, the quencher is removed from the DNA strand, leading to the initiation of fluorescence. The fluorescence resulting from cleaving the ribonucleotide and the quencher may be measured via any suitable technique.

The DNAzymes disclosed herein may be incorporated into a sensor. Generally, the sensor includes a matrix and one or more of the DNAzymes attached thereto. In an embodiment, the matrix is selected from gold particles, gold-coated substrates, and combinations thereof. In an embodiment, the arsenic sensor (incorporating an embodiment of the arsenic ion active DNAzymes disclosed herein) is capable of detecting an amount of $As^{5+}$ ranging from about 5 ppb to about 400 ppb. In another embodiment, the mercury sensor (incorporating an embodiment of the mercury ion active DNAzymes disclosed herein) is capable of detecting an amount of $Hg^{2+}$ ranging from about 2 ppb to about 8000 ppb.

In an embodiment of method for detecting a particular ion (e.g., mercury or arsenic), the DNAzyme portion of the sensor is contacted with a sample suspected of containing the particular ion (e.g., $Hg^{2+}$ or $As^{5+}$). When the specific metal ion contacts the DNAzyme, the ribonucleotide linkage is cleaved and the ribonucleotide and quencher are released, thereby initiating fluorescence. The amount of fluorescence produced is measured. The amount of fluorescence is compared to a control in which the specific ion is absent, and the change in fluorescence is indicative of the ion.

To further illustrate embodiment(s) of the present disclosure, various examples are given herein. It is to be understood that these examples are provided for illustrative purposes and are not to be construed as limiting the scope of the disclosed embodiment(s).

EXAMPLES

Novel mercury and arsenic active DNAzymes were created using the methods and materials described herein. The DNAzymes described in these examples may be suitable for use as sensors for detecting mercury or arsenic in a variety of samples.

Experimental Details

Synthesis of Oligonucleotides

Standard oligonucleotide pools (see FIG. 1) were prepared by automated DNA synthesis using cyanoethylphosphoramidite chemistry (Keck Biotechnology Laboratory, Yale University). Random-sequence DNA libraries were synthesized using an equimolar mixture of the four standard phosphoramidites (A, C, T, G). DNA oligonucleotides were purified by 10% preparative denaturing (8 M urea) polyacrylamide gel electrophoresis (PAGE). The purified oligonucleotide concentrations were determined spectroscopicallym and were calculated using the Biopolymer Calculator program.

Fluorescein and 4-(4-dimethylaminophenylazo)benzoic acid (DABCYL, the quencher) labels were incorporated into the DNA library during automated DNA synthesis using Fluorescein-dT amidite and DABCYL-dT amidite (Glen Research). The adenine ribonucleotide linkage was introduced during solid-state synthesis using A-TOM-CE Phosphoramidite (Glen Research).

The Fluorescein- and DABCYL-modified oligonucleotides were purified by reverse phase liquid chromatography (HPLC) performed on a Beckman Coulter HPLC System. Elution was achieved using a two-buffer system: (i) buffer A was 0.1 M triethylammonium acetate (TEAA, pH 6.5); (ii) and buffer B was pure acetonitrile. The TOM protective group on the 2'-hydroxyl group of the RNA linkage was removed by incubation with 100 µL of 1 M tetrabutylammonium fluoride (TBAF) in THF at 60° C. with shaking for 10 hours. 250 µL of 100 mM Tris (pH 8.3) was added, and incubation with shaking continued for about 30 minutes at 37° C.

The DNA was recovered using ethanol precipitation, and was dissolved in water containing 0.1% sodium dodecyl sulfate (SDS). The tetrabutylammonium salt was removed by centrifugation using a spin column (Nanosep 3K Omega, Pall Corp.).

Taq DNA polymerase, T4 DNA ligase, and T4 polynucleotide kinase (PNK) were purchased from Promega. All other chemical reagents were purchased from Sigma.

In Vitro Selection

5'-Phosphorylated, gel-purified, 90-nt (Pool-A, shown in FIG. 1) or 80-nt (Pool-B, shown in FIG. 1) random-sequence DNA 'X' (100 pmol) was mixed in an equimolar ratio with template 'T' and acceptor 'Y' (see FIG. 1). The mixture was heated to about 90° C. for about 30 seconds and cooled to room temperature. The mixture was combined with a ligase buffer and T4 DNA ligase for DNA ligation, in order to introduce the modified DNA domain. The ligation mixture (50 µL) contained 50 mM Tris-HCl, 40 mM NaCl, 10 mM MgCl2, 1 mg mL-1 BSA, 0.5 mM ATP, and 0.1 Weiss units µL-1 T4 DNA ligase. The solution was incubated at 23° C. for about 1 hour, and the ligated 109-nt DNA was purified by 10% denaturing PAGE.

The 123-nt (Pool-A) or 113-nt (Pool-B) DNA library constructed as above was used as the initial pool. The sequences were heated to 90° C. for about 30 seconds, cooled to room temperature, and then combined with a 2× selection buffer (100 mM HEPES, pH 6.8 at 23° C., 800 mM NaCl, 200 mM KCl, 15 mM $MgCl_2$, 10 mM $AsHNa_2O_4$, 2.5 mM $CdCl_2$, 2 mM $HgCl_2$, 0.5 mM $PbCl_2$) to a final DNA concentration of 100 nM. The mixture was incubated for self-cleavage at 23° C. for about 3 hours.

Lower concentrations of $As^{5+}$, $Pb^{2+}$, $Cd^{2+}$, and $Hg^{2+}$ were used, as the transition metal ions were found to be inhibitory on self-phosphorylating DNA. To minimize the potential inhibitory effect of these metal ions in this selection, they were used at their respective IC50 concentrations. In the case of $Mg^{2+}$, higher concentrations were used as it has been found that this metal does not inhibit the activity of the self-phosphorylating deoxyribozymes at concentrations as high as 25 mM (Wang et al., 2002).

As shown in FIG. 2, at step 1, a pool of single-stranded 90-nt or 80-nt DNAs containing random-sequence nucleotides was first ligated to the acceptor DNA 'Y' (23-nt) containing the three moieties: F (fluorophore; Fluorescein-dT), Ar (adenine ribonucleotide) and Q (quencher; DABCYL-dT). The ligated 123-nt or 113-nt DNA was purified by PAGE, as shown in step 2. The modified DNA molecules were incubated with several divalent metal ion cofactors for RNA cleavage, as shown in step 3. In the presence of particular metal ions, the enzyme carries out a catalytic reaction of the substrate strand at the scissile ribonucleic acid adenosine (rA) resulting in removal of the quencher molecule (Q) and initiation of fluorescence.

The fluorescence is measured using fluorescence spectroscopy. The selectivity of the DNAzyme was monitored by the change in fluorescence ($\lambda$excitation=490 nm and $\lambda$emission=520 nm).

Referring back to FIG. 2, any autocatalytic DNA capable of cleaving the lone RNA linkage was expected to generate either 102-nt or 92-nt DNA fragment that could be isolated by PAGE, as shown in step 4. The recovered DNA was then amplified by two successive polymerase chain reactions (PCR). As shown in step 5, the first PCR was carried out with the use of primers P1 and P2 (the sequences of which (for the respective pools) are shown in FIG. 1). The second PCR (step 6) used P1 and P3 (the sequences of which (for the respective pools) are shown in FIG. 1). Since P3 was a ribo-terminated primer, the double-stranded DNA product generated in the second PCR step contained a single ribonucleotide linkage in the deoxyribozyme containing strand. The DNA product from the second PCR was treated with NaOH (as shown in step 7) under conditions that could fully cleave the ribonucleotide linkage (0.25 M NaOH, 90° C., 10 minutes). The digested DNA mixture was subjected to PAGE purification and DNA phosphorylation (as shown in step 8).

DNA Phosphorylation was carried by incubation of purified DNA with 10 units of poly nucleotide kinase at 37° C. for about 1 hour for DNA phosphorylation in a 100 μL reaction mixture containing 50 mM Tris-HCl (pH 7.8), 40 mM NaCl, 10 mM $MgCl_2$, 1 mg $mL^{-1}$ BSA, and 0.84 μM ATP. 5'-phosphorylated DNA was further used to initiate the next round of selection.

Several cycles of selection and amplification were performed to isolate autocatalytic DNAzymes for specific metal ions by conducting the experiments in presence and absence of metal ions.

To facilitate the creation of DNAzymes, $Mg^{2+}$ and several transition metal ions were used, including $As^{5+}$, $Cd^{2+}$, $Pb^{2+}$, and $Hg^{2+}$ in the selection buffer. The total concentration of metal ions was chosen to be 15 mM with individual concentrations set at the following: 7.5 mM $Mg^{2+}$, 5 mM $As^{5+}$, 1.0 mM $Hg^{2+}$, 1.25 mM $Cd^{2+}$, 0.25 mM $Pb^{2+}$. The different pools were incubated with the same metal ions under similar conditions.

Kinetic Analysis of Xatalytic DNAzymes

All kinetic reactions involve the following steps: (1) heat denaturation of DNA in water for 30 seconds at 90° C., (2) incubation for RNA cleavage at room temperature in a reaction buffer for a designated time, (3) addition of EDTA to 30 mM to stop the reaction, (4) separation of cleavage products by denaturing 10% via PAGE, and (5) quantification using a Phospholmager and ImageQuant software.

Aliquots of an RNA cleavage reaction solution were collected at different reaction time points, and the rate constant for the reaction was determined by plotting the natural logarithm of the fraction of DNA that remains unreacted versus the reaction time (Santoro and Joyce, 1997). The negative slope of the line, obtained from points within the first 5-7% of the reaction and produced by a least-squares fit, was calculated as the rate constant.

Cloning and Sequencing

DNA sequences from the final rounds of selection were amplified by PCR and cloned into a vector by the TA cloning method. The plasmids containing individual catalysts were prepared using a Qiagen MiniPrep Kit. DNA sequencing was performed on a capillary DNA sequencer (Applied Biosystems—ABI 3730 DNA Analyzer), following the procedures recommended by the manufacturer.

Fluorescence Measurement

Fluorescence measurements were taken from 100 μL solutions on an HP (1046) fluorescence spectrophotometer. The excitation was set at 490 nm, and emission, at 520 nm. The background fluorescence was first measured by adding 100 μL buffer into the measurement cell.

RESULTS AND DISCUSSION

Two different starting pools each having 1015 single-stranded DNA molecules were generated, and the SELEX scheme (shown in FIG. 2) was used to select the target specific DNAzymes that are capable of catalyzing the RNA cleavage. The protocol developed by Mei et al., (2003) for the in vitro selection of RNA-cleaving DNA catalysts was used.

The RNA-cleaving DNAzymes were evolved under a different set of conditions. Due to the relative lability of the RNA bond toward hydrolytic cleavage, a ribonucleic adenosine was embedded in the DNA segment. The cleaved DNA was isolated by 10% denaturing via PAGE, after the cleavage reaction was stopped by the addition of EDTA (pH 8.0) to a final concentration of 30 mM. The isolated cleavage product was amplified by PCR (as mentioned earlier) in 50 μL reaction volume using primers P1 and P2. The amplified DNA product was used as the DNA template for a second PCR reaction using primer P1 and ribo-terminated primer P3. The procedures were the same for all selection cycles. The selection stringency was increased during the selection process by decreasing the reaction time and the concentration of available metal ions. A total of 15-25 selection and amplification cycles were carried out with each pool.

Selection Progress and Identification of Functional Sequences

The selection progress for the Pool-A sequences is summarized in FIG. 3. No detectable cleavage activity was observed for Pool-A sequences isolated in generations C0-C3 after a 3-hour incubation period. However, significant cleavage was seen in C5. By the C8 cycle, more than 32% of the DNA construct was cleaved after a 3-hour incubation. The $9^{th}$ cycle yielded a drastic increase in catalysis, shooting up to about 54% of total oligonucleotide pool. At this stage, three more cycles were evaluated to assess any further increase in cleavage efficiency; however, there was not an appreciable effect on ribosomal cleavage (data not shown).

The reaction time and presence/absence of metal ion was then progressively evaluated to isolate very efficient DNAzymes for specific metal ions. The self-cleavage reaction was first allowed to proceed for 10 minutes in C10 and 5 minutes in C11. The reaction time was further reduced to 1 minute in C12 and C13, to 10 seconds in C14 and C15, and finally to about 1 second in C16-C18. The DNA molecules in C19 were also allowed to react for 1 minute. The activity of the selected DNA dramatically decreased from 10 minutes of incubation (C10) to 1 minute of incubation (C12 & C13), leading to about 5% and 7% substrate cleavage, respectively. Further gradual decrease in incubation time to 5 seconds also produced minimal cleavage averaging about 1.5% over three generations (C16-C18).

The incubation time was then increased to 1 minute (C19), resulting in a 50% cleavage efficiency. DNA sequences from the 19th cycle (C19) were amplified by PCR and cloned into a vector by the TA cloning method. The plasmids containing the individual catalysts were prepared using a Quiagen Mini-Prep kit and sequenced. The population of molecules obtained after selection and reselection showed surprising similarity in their sequences when they were evolved using in vitro selection.

The sequences of 27 individual clones revealed a diverse combination of functional motifs and are classified into three major families (FIGS. 4A, 4C and 4E) based on sequence similarities. Of 27 mercury-active sequences, 16 fell in to one family (Family-Im (SEQ ID NOS: 13-28), FIG. 4A), most of which exhibited 'AATTCCGTAGGTCCAGTG' (SEQ ID NO: 68) as a conserved region. The remaining 11 sequences are classified in two different families of seven and four sequences, respectively (Family—IIm (SEQ ID NOS: 30-36) & IIIm (SEQ ID NOS: 38-41), FIGS. 4C and 4E, respectively). A secondary structure (SEQ ID NOS: 29, 37, 42) for the above mentioned sequence (most common structural motif, shown in FIG. 4B) was predicted by the M-fold program (Zuker, 2003). On the basis of this structure, a trans-cleaving enzyme (referred to as Mer-27 (SEQ ID NO: 28) in FIG. 4A) was designed, and was further examined for its metal ion specificity and kinetics. Most of these sequences were found to be more highly active in the presence of $Hg^{2+}$ than in the presence of Mg , As , Cd or Pb when tested individually.

The confirmation of its catalytic activity and the specificity was established in the following experiments. The results obtained from Pool-B sequences (see FIG. 5) were found to be different from what was noticed with Pool-A. No cleavage was observed until the $8^{th}$ cycle (C8), and the cleavage progressively increased to 18% at C11 without further improvement even after three more cycles (C12-C14).

When the incubation time was reduced to 10 minutes (C15), 5 minutes (C16), 1 minutes (C17-C18), 10 seconds (C19-C20), and finally 1 second (C21-C22), a decrease in ribosomal cleavage to 2% was noticed at the lowest incubation time (1 second). When increased to 1 minute in the $23^{rd}$ cycle, an increase in ribosomal cleavage to 14% was observed (similar to Pool-A).

DNA sequences from the $23^{rd}$ generation were amplified, cloned into a vector by the TA cloning method, and sequenced as mentioned earlier. The functional molecules for Pool-B obtained from M-fold program (after selection and reselection) showed minimal dissimilarity leading to two families (Families Ia (SEQ ID NOS: 43-54) and IIa (SEQ ID NOS: 56-60) respectively shown in FIGS. 6A and 6C) based on sequence similarities. The sequences of 17 individual clones revealed a major conserved motive 'ATCTCCTCCTGTTC' (SEQ ID NO: 62) found in 12 clones (see FIG. 6A). The remaining five clones fell into one family (see FIG. 6C). The most common structural motif (referred to as Ars-17 (SEQ ID NO: 54) in FIG. 6A) was engineered into a transcleaving enzyme as mentioned above, and examined further for its metal ion specificity and kinetics.

The activities found in both pools were lost once the respective metal ions were omitted from the reaction mixture.

In vitro selection techniques rely on the probability that some DNA molecules in a random sequence library fold into an appropriate tertiary structure with lowest possible energy, and catalyze a desired reaction (e.g., 'RNA cleaving'). Catalytic activity is derived from the, formation of 2',3'-cyclic phosphate and 5'-hydroxyl RNA termini from the RNA 2' hydroxyl group on the adjacent phosphodiester linkage. Considering the probability that one or more DNA molecules in a vast random-sequence pool will possess some catalytic propensity for a given chemical transformation, the extent of sequence diversity in the DNA pool may have a profound effect on the final outcome of the experiment. Without sufficient sequence diversity, the probability of finding a proficient DNAzyme may be low. Thus, sufficient sequence diversity in the DNA pool (and hence more catalytic DNA sequences) is beneficial for achieving isolation of efficient deoxyribozymes. The catalytic sequence diversity established by in vitro selection is governed largely by the choice of selection pressures, one of which is the length of the reaction time. Schlosser and Li (2004) examined the effect of reaction stringency (in terms of shortening of the reaction time) during in vitro selection of RNA-cleaving DNAzymes, and found a logarithmic decrease in sequence diversity with decrease in reaction time. In vitro selection of RNA-cleaving DNAzymes in Schlosser and Li's study resulted in 43 sequences in a 5-hour reaction period, as compared to 8 sequences when the reaction period was decreased to 5 seconds. In contrast, the present inventors found 27 and 17 different sequences for mercury (II) (SEQ ID NOS: 13-28, 30-36, 38-41) and arsenic (V) (SEQ ID NOS: 43-54, 56-60), respectively, when incubated for a 1 second reaction time, indicating efficient selection and higher sequence diversity.

Catalytic Activity and Metal Ion Specificities

In vitro selected nucleic acid enzymes were previously found to be active in the presence of metal ions other than the metal ions used during selection (Faulhammer and Famulok 1997; Li et al., 2000). The examples disclosed herein demonstrate that divalent metal ions are necessary for the activity of RNA cleavage, as no more than 0.8% of the substrate was cleaved after 50 hours in the presence of 100 µM EDTA.

Figure 7:
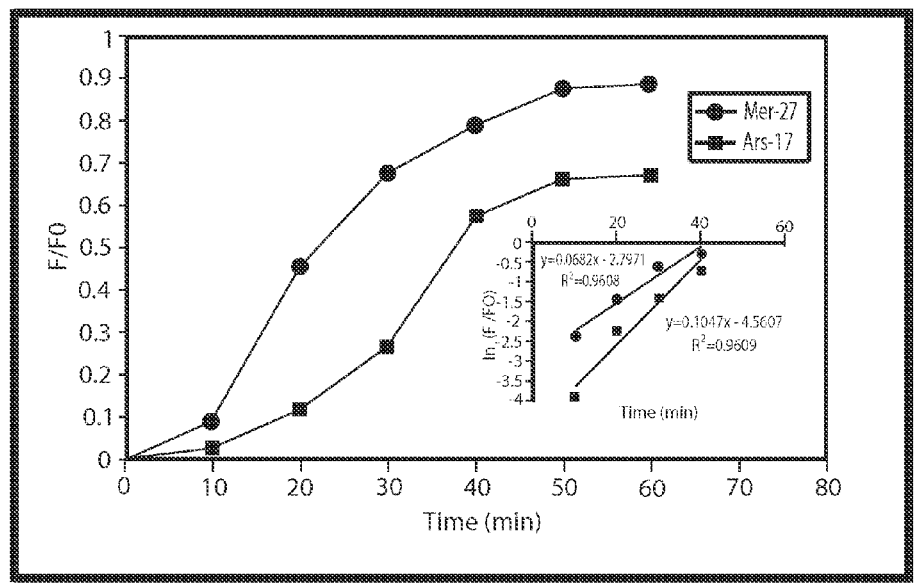
FIG. 7 is a graph depicting the kinetics of ribosomal cleavage activity of sequences Mer-27 (see FIG. 4A—SEQ ID NO: 28) and Ars-17 (see FIG. 6A—SEQ ID NO: 54), the assays were conducted with 100 µM $Hg^{2+}$ (for Mer-27 (SEQ ID NO: 28)) and $As^{5+}$ (for Ars-17 (SEQ ID NO: 54)) in 100 mM HEPES buffer at pH 7.0.

To further investigate this catalytic activity and the cleavage specificity, two selected DNAzymes, Mer-27 (SEQ ID NO: 28) and Ars-17 (SEQ ID NO: 54), were assayed in the presence of different metal ions. These cloned mercury-active and arsenic-active sequences were randomly chosen and sampled for self-cleavage activity. Under the in vitro selection conditions mentioned above, highly abundant Mer-27 (SEQ ID NO: 28) and Ars-17 (SEQ ID NO: 54) were individually examined and they showed high cleavage activity against the target metal species (0.09 $min^{-1}$ and 0.05 $min^{-1}$, respectively). These two cloned sequences were found at highest frequency of occurrence in their respective pools. Further, these DNAzymes were characterized in terms of their catalytic rate by conducting the experiments with individual metal ions. The catalytic rates of Mer-27 (SEQ ID NO: 28) and Ars-17 (SEQ ID NO: 54) (in the presence of their target metal $Hg^{2+}$ and $As^{5+}$ are presented in FIG. 7 in terms of fluorescence relative to background values (F/F0). Similar plots were obtained for all metal ions to derive the first order reaction rate (min−1) and the catalytic rates range from 0.006 $min^{-1}$ to 0.01 $min^{-1}$.

The following activity trends were observed based on the data presented in Table 1.

Mer-27:$Hg^{2+}$>>$Cu^{2+}$~$Zn^{2+}$>$Pb^{2+}$~$Cd^{2+}$>$Ni^{2+}$>$Mg^{2+}$~$Ca^{2+}$22 $Pd^{2+}$~$As^{5+}$Ars-17:$As^{5+}$$Cd^{2+}$$Hg^{2+}$$Pb^{2+}$>$Cu^{2+}$>$Zn^{2+}$>$Ni^{2+}$$Mg^{2+}$~$Ca^{2+}$>$Pd^{2+}$

TABLE 1

Metal Ion Activity for Mer-27 and Ars-17

| Metal ion | $K_{obs}$ (min$^{-1}$) Mer-27 (SEQ ID NO: 28) | $K_{obs}$ (min$^{-1}$) Ars-17 (SEQ ID NO: 54) |
| --- | --- | --- |
| $Hg^{2+}$ | 1.90 | 0.5 |
| $Cu^{2+}$ | 1.22 | 0.35 |
| $Zn^{2+}$ | 1.15 | 0.1 |
| $Pb^{2+}$ | 0.55 | 0.46 |
| $Cd^{2+}$ | 0.5 | 0.99 |
| $Ni^{2+}$ | 0.21 | 0.05 |
| $Mg^{2+}$ | 0.02 | 0.01 |
| $Ca^{2+}$ | 0.022 | 0.007 |
| $As^{5+}$ | 0.007 | 1.15 |
| $Pd^{2+}$ | 0.01 | 0.004 |

The degree of dissimilarity observed for the two different pools examined under similar conditions was surprising considering that selection was carried out under the same combinations of metal ions. At 100 µM concentration, Mer-27 (SEQ ID NO: 28) showed highest activity in presence of $Hg^{2+}$ followed by $Cu^{2+}$, and Ars-17 (SEQ ID NO: 54) was found to be highly active in presence of $As^{5+}$ followed by $Cd^{2+}$.

The high selectivity of other mercury-selective sequences towards $Hg^{2+}$ followed by $Cu^{2+}$ has been described elsewhere. Nolan and Lippard (2003) reported an in vitro selection protocol for the development of fluorescent sensors for mercuric ion in presence of other ions with the exception of $Cu^{2+}$, which effectively competed with $Hg^{2+}$ binding. Thomas et al. (2004) studied the inhibition of mercuric ion on the cleavage rate of an imidazole modified, $M^{2+}$-dependent self-cleaving $9_{25}$-11 DNA system. They found that inhibition of cleavage is highly selective in presence of $Hg^2$ with the exception of Cu Table 1 indicates that arsenic-active DNAzymes were also found to exhibit reasonably high activity in presence of $Cd^{2+}$. Other sequences having multiple metal ion activity have been reported earlier. For example, the 8-17 DNAzyme selected from solutions containing $Mg^{2+}$ (Santoro and Joyce, 1997), also exhibited activity against $Mg^{2+}$/Histidine (Faulhammer and Famulok, 1997) and 100 µM $Zn^{2+}$ (Li et al., 2000). However, it was shown to be the most active in the presence of $Pb^{2+}$, with activity decreasing in the following order: $Pb^{2+}$>$Zn^{2+}$>$Ca^{2+}$>$Mg^{2+}$. Similarly, Liu et al. (2003) studied the activity of a DNAzyme (DEC22-18) selected using $Co^{2+}$ against other metals, and noticed that it is highly active in the presence of $Mn^{2+}$, $Cd^{2+}$ and $Ni^{2+}$ as well. The versatility of metallodeoxyribozymes may be attributable to the fact that metal solutions are contaminated with trace quantities of non-targeted metals with similar ionic radii and pKa values in water for their respective hydrated forms. Yet, this correlation is not noticed with all metal ions studied. Similar results have been reported for hammerhead ribozymes (Dahm et al., 1993), 10-23 deoxyribozymes (Santoro and Joyce, 1998) and 17E deoxyribozyme (Li et al., 2000).

In addition to playing structural roles in the DNAzyme, the DNAzyme activity may also be influenced by the direct involvement of the divalent metal ions in chemical reactions. For example, the metal hydride can act as a general base and deprotonate the 2'-hydroxyl at the cleavage site. Alternatively, the metal ion can serve as a Lewis acid by direct coordination to the oxygen of 2'-hydroxyl, thereby weakening the 2'-O—H bond (Silverman, 2004). Metal ions may further coordinate to the non-bridging phosphodiester oxygen to either make the phosphorus center more susceptible to nucleophilic attack, or help stabilize the developing negative charge of the oxy-anion in the trigonal-bipyramidal transition state. In addition, direct coordination of divalent metal ions to the 5'-oxygen leaving group will stabilize the developing negative charge and accelerate the cleavage of 5'-O—P bond. The inverse correlation between the pKa value of the metal ligands and the ribosomal cleavage efficiency of Mer-27 (SEQ ID NO: 28) and Ars-17 (SEQ ID NO: 54) provides evidence that metal ions play some of the catalytic roles.

In summary, Pool-A resulted in the selection of highly mercury-active sequences, while Pool-B was found to produce arsenic-active sequences. The transition metals are generally favored over alkaline earth metals. This increased preference of transition metal ions over alkaline earth metals may indicate differences in the metal binding sites on the DNAzymes, including the binding affinity, ligand-set, ionic-radii and geometry as reported by Bruesehoff et al. (2002). Alkaline earth metal ions tend to maintain their hydration state and bind nucleic acids through outer-sphere coordination with low to moderate binding affinity (Holbrook et al., 1977). However, transition metal ions like $Zn^{2+}$, $Co^{2+}$, $Mn^{2+}$ and $Cd^{2+}$ can bind to both the non-bridging phosphate oxygen and the O or N groups on the nucleic acid bases using either inner-sphere or outer-sphere coordination.

Concentration Dependency

Figure 8:
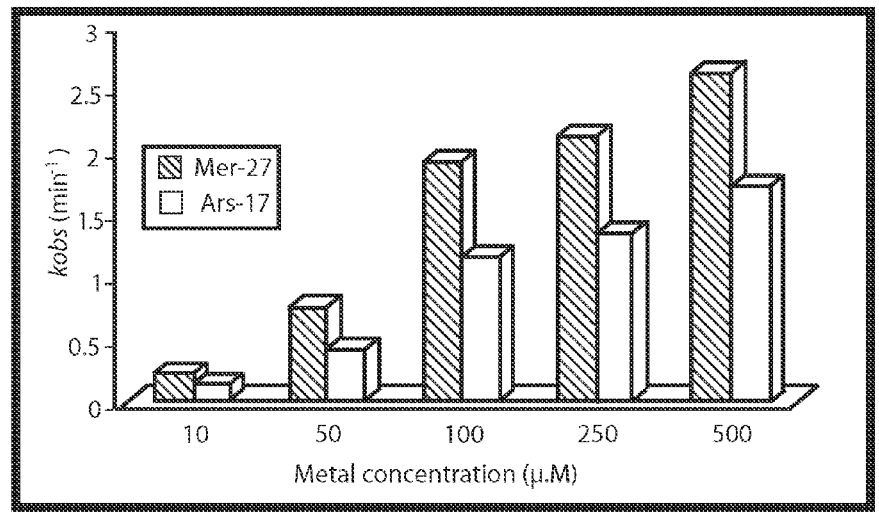
FIG. 8 is a graph depicting the concentration dependent activity of Mer-27 (SEQ ID NO: 28) and Ars-17 (SEQ ID NO: 54) with varying concentrations of $Hg^{2+}$ and $As^{5+}$, respectively, the assays were conducted with 100 mM in 100 mM HEPES buffer at pH 7.0.

The effect of metal ion concentration on the catalytic cleavage by Mer-27 (SEQ ID NO: 28) and Ars-17 (SEQ ID NO: 54) was examined by conducting the experiments with increasing metal ion concentrations (10 µM-500 µM). FIG. 8 indicates that the Mer-27 (SEQ ID NO: 28) cleavage rate increases 10-fold, from 0.3 min$^{-1}$ to 2.7 min$^{-1}$, while the Ars-17 (SEQ ID NO: 54) rate increased from 0.19 min$^{-1}$ to 1.7 min$^{-1}$. The rates observed at the highest concentration evaluated (500 µM) are in agreement with earlier reported literature values for other mercury and arsenic selective sequences (Liu et al., 2003; Ting et al., 2004). Liu et al. (2003) studied a variety of RNA-cleaving DNAzymes at different pH and found that the most of them showed fairly large rate constants ranging from 0.2 to 1.3 min$^{-1}$. Particularly, the Mer-27 (SEQ ID NO: 28) is one of the fastest DNAzymes reported to date. Without being bound to any theory, it is believed that the significantly high cleavage activity is due to the balanced and appropriately positioned metal binding sites on the DNAzyme, or the preference of metal ions with a favorable pKa of metal bound water for the DNAzyme, or a better Lewis acidity of metal DNAzyme interaction, or combinations thereof (i.e., one by one or all together) in random or in organized fashion. Whether the previous factors occur one by one in a random or organized fashion may depend, at least in part, on the lowest energy product/configuration in between the metal and the DNAzyme molecule. The ultimate interaction of metal and DNAzyme leads to the lowest energy configuration that catalyzes/cleaves the ribonucleic acid molecule embedded in the DNA.

The formation of an RNA 2',3'-cyclic phosphate via intramolecular cleavage is relatively easy without catalysis, as incubations of an RNA strand under basic conditions lead to random scission along the entire length of the strand.

The experiments performed herein used unmodified nucleotides for selection of DNAzymes. Nolan and Lippard (2003) developed a water-soluble, turn-on sensor using sulfur incorporated (3,9-dithia-6-azaundacane moiety) DNA pool that exhibits high selectivity and sensitivity for Hg (II). Similarly, Thomas et al. (2004) selected high affinity DNAzyme-based ligand for sensing $Hg^{2+}$ using imidazole modified DNA. As disclosed herein, routine DNA material (having no such modifications) may be used for the development of highly selective and specific DNAzymes for mercury (II) and arsenic (V).

The isolation of distinct families of DNAzymes that recognize $Hg^{2+}$ and $As^{5+}$ resulted in the emergence of new functional motifs with relatively high catalytic rates (2.6 $min^{-1}$ for Mer-27 (SEQ ID NO: 28) and 1.7 $min^{-1}$ for Ars-17 (SEQ ID NO: 54)). These DNAzymes may advantageously be incorporated into biosensors for detecting the specific metals in a variety of samples.

While several embodiments have been described in detail, it will be apparent to those skilled in the art that the disclosed embodiments may be modified. Therefore, the foregoing description is to be considered exemplary rather than limiting.

What is claimed is:

1. A self-cleaving, arsenic ion-activated DNAzyme, comprising: a nucleotide sequence including a base sequence selected from ATCTCCTCCTGTTC (SEQ ID NO: 62), ATCTGCTCCTGTTC (SEQ ID NO: 63), ATCTCCTCATGTTC (SEQ ID NO: 64), ATCTCCTCTTGTTC (SEQ ID NO: 65), ATCTCCAACCTGTTC (SEQ ID NO: 66), and CCGTAGCGCAAAT (SEQ ID NO: 67), and having a secondary structure that allows recognition of an arsenic ion.

2. The arsenic ion-activated, DNAzyme as defined in claim 1 wherein the arsenic ion is $As^{5+}$.

3. The arsenic ion-activated DNAzyme, as defined in claim 1 wherein the nucleotide sequence is selected from SEQ ID NOS: 43-46, 47-54, and 56-60.

4. The arsenic ion-activated DNAzyme, as defined in claim 1, further comprising: a fluorophore attached to the nucleotide sequence at its 3' or 5' end; a ribonucleotide attached to the fluorophore; and a quencher of the fluorophore attached to the ribonucleotide.

5. The arsenic ion-activated DNAzyme, as defined in claim 4 wherein the fluorophore is selected from fluoroscein, fluoroscein substitutes, long wavelength dyes, and UV-excited fluorophores, and wherein the quencher is configured to absorb energy of an excited fluorophore.

6. An arsenic ion sensor, comprising: a matrix; and a self-cleaving arsenic ion-activated DNAzyme attached to the matrix, the DNAzyme including a nucleotide sequence having a base sequence selected from ATCTCCTCCTGTTC (SEQ ID NO: 62), ATCTGCTCCTGTTC (SEQ ID NO: 63), ATCTCCTCATGTTC (SEQ ID NO: 64), ATCTCCTCT-TGTTC (SEQ ID NO: 65), ATCTCCAACCTGTTC (SEQ ID NO: 66), and CCGTAGCGCAAAT (SEQ ID NO: 67) and having a secondary structure that allows recognition of an arsenic ion.

7. The sensor as defined in claim 6 wherein the matrix is selected from gold particles, gold-coated substrates, and combinations thereof.

8. The sensor as defined in claim 6 wherein the arsenic ion is $As^{5+}$.

9. The sensor as defined in claim 8 wherein the sensor is capable of detecting an amount of $As^{5+}$ ranging from about 5 ppb to about 400 ppb.

10. The sensor as defined in claim 6 wherein the nucleotide sequence is selected from SEQ ID NOS: 43-46, 47-54, and 56-60.

11. A method of detecting a presence of arsenic, comprising contacting a DNAzyme with a sample suspected of containing $As^{5+}$, the DNAzyme having a single nucleic acid strand including a fluorophore separated from a quencher of the fluorophore via a ribonucleotide, the DNAzyme capable of fluorescing in the presence of $As^{5+}$; and measuring an amount of fluorescence produced; wherein the DNAzyme is a self-cleaving arsenic ion-activated, DNAzyme including a base sequence selected from ATCTCCTCCTGTTC (SEQ ID NO: 62), ATCTGCTCCTGTTC (SEQ ID NO: 63), ATCTC-CTCATGTTC (SEQ ID NO: 64), ATCTCCTCTTGTTC (SEQ ID NO: 65), ATCTCCAACCTGTTC (SEQ ID NO: 66), and CCGTAGCGCAAAT (SEQ ID NO: 67).

* * * * *

SEQUENCE LISTING

```
<160> NUMBER OF SEQ ID NOS: 72

<210> SEQ ID NO 1
<211> LENGTH: 18
<212> TYPE: DNA
<213> ORGANISM: Artificial Sequence
<220> FEATURE:
<221> NAME/KEY: modified_base
<222> LOCATION: 10, 11, 12
<223> OTHER INFORMATION: synthetic
      modified base 11: ribonucleotide [any nucleotide]

<400> SEQUENCE: 1
ggtctgtccn nntgtcga                                               18

<210> SEQ ID NO 2
<211> LENGTH: 72
<212> TYPE: DNA
<213> ORGANISM: Artificial Sequence
<220> FEATURE:
<221> NAME/KEY: modified_base
<222> LOCATION: 10..54
<223> OTHER INFORMATION: synthetic
      modified bases: [any nucleotide may be present/absent]

<400> SEQUENCE: 2
tccgtaaagn nnnnnnnnnn nnnnnnnnnn nnnnnnnnnn nnnnnnnnnn nnnngcacga    60
cgaggtttac ac                                                       72

<210> SEQ ID NO 3
<211> LENGTH: 28
<212> TYPE: DNA
<213> ORGANISM: Artificial Sequence
<220> FEATURE:
<223> OTHER INFORMATION: synthetic

<400> SEQUENCE: 3
ccagacagga taacagctag gcatttcg                                     28

<210> SEQ ID NO 4
<211> LENGTH: 18
<212> TYPE: DNA
<213> ORGANISM: Artificial Sequence
<220> FEATURE:
<223> OTHER INFORMATION: Pool A primer 1

<400> SEQUENCE: 4
gtgtaaacct cgtcgtgc                                                18

<210> SEQ ID NO 5
<211> LENGTH: 27
<212> TYPE: DNA
<213> ORGANISM: Artificial Sequence
<220> FEATURE:
<223> OTHER INFORMATION: Pool A primer 2
```

```
<400> SEQUENCE: 5
ggtctgtcca tatgtcgatc cgtaaag                                              27

<210> SEQ ID NO 6
<211> LENGTH: 18
<212> TYPE: DNA
<213> ORGANISM: Artificial Sequence
<220> FEATURE:
<221> NAME/KEY: modified_base
<222> LOCATION: 18
<223> OTHER INFORMATION: Pool A primer 3
      modified base 18: ribonucleotide [any nucleotide]

<400> SEQUENCE: 6
ggtctgtcca tatgtcgn                                                        18

<210> SEQ ID NO 7
<211> LENGTH: 18
<212> TYPE: DNA
<213> ORGANISM: Artificial Sequence
<220> FEATURE:
<221> NAME/KEY: modified_base
<222> LOCATION: 10, 11, 12
<223> OTHER INFORMATION: synthetic
      modified base 11: ribonucleotide [any nucleotide]

<400> SEQUENCE: 7
ggtctgtccn nntgtcga                                                        18

<210> SEQ ID NO 8
<211> LENGTH: 62
<212> TYPE: DNA
<213> ORGANISM: Artificial Sequence
<220> FEATURE:
<221> NAME/KEY: modified_base
<222> LOCATION: 10..44
<223> OTHER INFORMATION: synthetic
      modified bases: [any nucleotide may be present/absent]

<400> SEQUENCE: 8
tccgtaaagn nnnnnnnnn nnnnnnnnnn nnnnnnnnnn nnnngcacga cgaggtttac           60
ac                                                                         62

<210> SEQ ID NO 9
<211> LENGTH: 28
<212> TYPE: DNA
<213> ORGANISM: Artificial Sequence
<220> FEATURE:
<223> OTHER INFORMATION: synthetic

<400> SEQUENCE: 9
ccagacagga taacagctag gcatttcg                                             28

<210> SEQ ID NO 10
<211> LENGTH: 18
<212> TYPE: DNA
<213> ORGANISM: Artificial Sequence
<220> FEATURE:
<223> OTHER INFORMATION: Pool B primer 1

<400> SEQUENCE: 10
gtgtaaacct cgtcgtgc                                                        18

<210> SEQ ID NO 11
<211> LENGTH: 27
<212> TYPE: DNA
```

```
<213> ORGANISM: Artificial Sequence
<220> FEATURE:
<223> OTHER INFORMATION: Pool B primer 2

<400> SEQUENCE: 11
ggtctgtcca tatgtcgatc cgtaaag                                           27

<210> SEQ ID NO 12
<211> LENGTH: 18
<212> TYPE: DNA
<213> ORGANISM: Artificial Sequence
<220> FEATURE:
<221> NAME/KEY: modified_base
<222> LOCATION: 18
<223> OTHER INFORMATION: Pool B primer 3
      modified base 18: ribonucleotide [any nucleotide]

<400> SEQUENCE: 12
ggtctgtcca tatgtcgn                                                     18

<210> SEQ ID NO 13
<211> LENGTH: 44
<212> TYPE: DNA
<213> ORGANISM: Artificial Sequence
<220> FEATURE:
<223> OTHER INFORMATION: synthetic

<400> SEQUENCE: 13
ggacctacgg ttcagtaatt ccgtaggtcc agtgccgctt acgt                        44

<210> SEQ ID NO 14
<211> LENGTH: 43
<212> TYPE: DNA
<213> ORGANISM: Artificial Sequence
<220> FEATURE:
<223> OTHER INFORMATION: synthetic

<400> SEQUENCE: 14
aggattgggg tcagtaattc cgtaggtcca gtgacgctta cta                         43

<210> SEQ ID NO 15
<211> LENGTH: 44
<212> TYPE: DNA
<213> ORGANISM: Artificial Sequence
<220> FEATURE:
<223> OTHER INFORMATION: synthetic

<400> SEQUENCE: 15
attgttaccg tacagtaatt ccgtcggtcc agtgccgctt acgc                        44

<210> SEQ ID NO 16
<211> LENGTH: 43
<212> TYPE: DNA
<213> ORGANISM: Artificial Sequence
<220> FEATURE:
<223> OTHER INFORMATION: synthetic

<400> SEQUENCE: 16
acacttgccg taacgtaatt ccgtaggtcc agtgccgcgg aca                         43

<210> SEQ ID NO 17
<211> LENGTH: 44
<212> TYPE: DNA
<213> ORGANISM: Artificial Sequence
<220> FEATURE:
<223> OTHER INFORMATION: synthetic
```

-continued

<400> SEQUENCE: 17
acgcttattg tcacgtaatt ccgtaggtcc agtggcgctt acgg        44

<210> SEQ ID NO 18
<211> LENGTH: 44
<212> TYPE: DNA
<213> ORGANISM: Artificial Sequence
<220> FEATURE:
<223> OTHER INFORMATION: synthetic

<400> SEQUENCE: 18
aagcttacaa tctcgtaatt ccgtaggtcc agtgccgctt acgc        44

<210> SEQ ID NO 19
<211> LENGTH: 43
<212> TYPE: DNA
<213> ORGANISM: Artificial Sequence
<220> FEATURE:
<223> OTHER INFORMATION: synthetic

<400> SEQUENCE: 19
aggcttaccc tccctaattc cgtaggtcca gtgccgctta cgt        43

<210> SEQ ID NO 20
<211> LENGTH: 43
<212> TYPE: DNA
<213> ORGANISM: Artificial Sequence
<220> FEATURE:
<223> OTHER INFORMATION: synthetic

<400> SEQUENCE: 20
agcctgacct tcccgaattc cgtaggtcca gtgacgagta cgt        43

<210> SEQ ID NO 21
<211> LENGTH: 43
<212> TYPE: DNA
<213> ORGANISM: Artificial Sequence
<220> FEATURE:
<223> OTHER INFORMATION: synthetic

<400> SEQUENCE: 21
aattttaccg tcccgaattc cgtaggtcca gtgccgctta cgt        43

<210> SEQ ID NO 22
<211> LENGTH: 43
<212> TYPE: DNA
<213> ORGANISM: Artificial Sequence
<220> FEATURE:
<223> OTHER INFORMATION: synthetic

<400> SEQUENCE: 22
acttaccgta gggtgaattc cgtaggtcca gtgccgctta cgt        43

<210> SEQ ID NO 23
<211> LENGTH: 44
<212> TYPE: DNA
<213> ORGANISM: Artificial Sequence
<220> FEATURE:
<223> OTHER INFORMATION: synthetic

<400> SEQUENCE: 23
aggcttaccg tcccgtaatt ccgtaggtcc agtgccgctt acgt        44

<210> SEQ ID NO 24
<211> LENGTH: 44

```
<212> TYPE: DNA
<213> ORGANISM: Artificial Sequence
<220> FEATURE:
<223> OTHER INFORMATION: synthetic

<400> SEQUENCE: 24
aatcttaccg ttacgtaatt ccgtaggtcc agtgcggcct tacg            44

<210> SEQ ID NO 25
<211> LENGTH: 44
<212> TYPE: DNA
<213> ORGANISM: Artificial Sequence
<220> FEATURE:
<223> OTHER INFORMATION: synthetic

<400> SEQUENCE: 25
atgcttacgc tagcgtaatt ccgtaggtcc agtgccgctt gcgt            44

<210> SEQ ID NO 26
<211> LENGTH: 44
<212> TYPE: DNA
<213> ORGANISM: Artificial Sequence
<220> FEATURE:
<223> OTHER INFORMATION: synthetic

<400> SEQUENCE: 26
acgcttaccg tcccgtaatt ccgccggtcc agtgcaagct tacc            44

<210> SEQ ID NO 27
<211> LENGTH: 44
<212> TYPE: DNA
<213> ORGANISM: Artificial Sequence
<220> FEATURE:
<223> OTHER INFORMATION: synthetic

<400> SEQUENCE: 27
atccttaccg tcccgtaatt ccgtaggtcc agtgcagctt atga            44

<210> SEQ ID NO 28
<211> LENGTH: 44
<212> TYPE: DNA
<213> ORGANISM: Artificial Sequence
<220> FEATURE:
<223> OTHER INFORMATION: synthetic

<400> SEQUENCE: 28
actcttacaa tcccgtaatt ccgtaggtcc agtgcggctt aagt            44

<210> SEQ ID NO 29
<211> LENGTH: 44
<212> TYPE: DNA
<213> ORGANISM: Artificial Sequence
<220> FEATURE:
<223> OTHER INFORMATION: synthetic

<400> SEQUENCE: 29
ggacctacgg ttcagtaatt ccgtaggtcc agtgccgctt acgt            44

<210> SEQ ID NO 30
<211> LENGTH: 44
<212> TYPE: DNA
<213> ORGANISM: Artificial Sequence
<220> FEATURE:
<223> OTHER INFORMATION: synthetic

<400> SEQUENCE: 30
```
aggcttaccg tcccgtggtt ccgagtctcg cgtgacgctt acgt          44

<210> SEQ ID NO 31
<211> LENGTH: 44
<212> TYPE: DNA
<213> ORGANISM: Artificial Sequence
<220> FEATURE:
<223> OTHER INFORMATION: synthetic

<400> SEQUENCE: 31
aaacttaccc tcacgtggtt ccgagtctcg cgtgacgctt acgt          44

<210> SEQ ID NO 32
<211> LENGTH: 44
<212> TYPE: DNA
<213> ORGANISM: Artificial Sequence
<220> FEATURE:
<223> OTHER INFORMATION: synthetic

<400> SEQUENCE: 32
aggcttactt tctcgtggtt ccgagtctcg cgtgccgctt acgt          44

<210> SEQ ID NO 33
<211> LENGTH: 44
<212> TYPE: DNA
<213> ORGANISM: Artificial Sequence
<220> FEATURE:
<223> OTHER INFORMATION: synthetic

<400> SEQUENCE: 33
attcggaccg tcggtggttc cgagtctcgc gtgcccgtat acgt          44

<210> SEQ ID NO 34
<211> LENGTH: 44
<212> TYPE: DNA
<213> ORGANISM: Artificial Sequence
<220> FEATURE:
<223> OTHER INFORMATION: synthetic

<400> SEQUENCE: 34
acgctcaccg tcccgggttc cgagtctcgc gtgccgctta cgtc          44

<210> SEQ ID NO 35
<211> LENGTH: 44
<212> TYPE: DNA
<213> ORGANISM: Artificial Sequence
<220> FEATURE:
<223> OTHER INFORMATION: synthetic

<400> SEQUENCE: 35
atgcatatcg accgtggttc cgagtctcgc gtgccgctta cgtc          44

<210> SEQ ID NO 36
<211> LENGTH: 44
<212> TYPE: DNA
<213> ORGANISM: Artificial Sequence
<220> FEATURE:
<223> OTHER INFORMATION: synthetic

<400> SEQUENCE: 36
acgcttacaa ttagccggtt ccgagtctcg cgtgcaactt aagt          44

<210> SEQ ID NO 37
<211> LENGTH: 44
<212> TYPE: DNA
<213> ORGANISM: Artificial Sequence
<220> FEATURE:
<223> OTHER INFORMATION: synthetic

<400> SEQUENCE: 37
aggcttaccg tcccgtggtt ccgagtctcg cgtgacgctt acgt          44

<210> SEQ ID NO 38
<211> LENGTH: 43
<212> TYPE: DNA
<213> ORGANISM: Artificial Sequence
<220> FEATURE:
<223> OTHER INFORMATION: synthetic

<400> SEQUENCE: 38
aggcttatcg tggcgcgttc aaaaggggca ctgccgctta cgt          43

<210> SEQ ID NO 39
<211> LENGTH: 43
<212> TYPE: DNA
<213> ORGANISM: Artificial Sequence
<220> FEATURE:
<223> OTHER INFORMATION: synthetic

<400> SEQUENCE: 39
attcttagcg tacgtcgttc aaaggggca ctgccgctta cgt           43

<210> SEQ ID NO 40
<211> LENGTH: 43
<212> TYPE: DNA
<213> ORGANISM: Artificial Sequence
<220> FEATURE:
<223> OTHER INFORMATION: synthetic

<400> SEQUENCE: 40
acgcttaacg tccaacgttc aaaaggggca ctgccaatta cgt          43

<210> SEQ ID NO 41
<211> LENGTH: 43
<212> TYPE: DNA
<213> ORGANISM: Artificial Sequence
<220> FEATURE:
<223> OTHER INFORMATION: synthetic

<400> SEQUENCE: 41
atgcttaccg tcctttcgtt caaaaggggc actgccgctt acg          43

<210> SEQ ID NO 42
<211> LENGTH: 43
<212> TYPE: DNA
<213> ORGANISM: Artificial Sequence
<220> FEATURE:
<223> OTHER INFORMATION: synthetic

<400> SEQUENCE: 42
aggcttatcg tggcgcgttc aaaaggggca ctgccgctta cgt          43

<210> SEQ ID NO 43
<211> LENGTH: 44
<212> TYPE: DNA
<213> ORGANISM: Artificial Sequence
<220> FEATURE:
<223> OTHER INFORMATION: synthetic

<400> SEQUENCE: 43
ggacctacgg ttcagtatct cctcctgttc ggttgccgct tacg         44

<210> SEQ ID NO 44
<211> LENGTH: 42
<212> TYPE: DNA
<213> ORGANISM: Artificial Sequence
<220> FEATURE:
<223> OTHER INFORMATION: synthetic

<400> SEQUENCE: 44
agcattgggg tcagtatctc ctcctgttcc ggacgcttac ta        42

<210> SEQ ID NO 45
<211> LENGTH: 44
<212> TYPE: DNA
<213> ORGANISM: Artificial Sequence
<220> FEATURE:
<223> OTHER INFORMATION: synthetic

<400> SEQUENCE: 45
gcgtcaaccg tacagtatct gctcctgttc gagaaccgct tacg        44

<210> SEQ ID NO 46
<211> LENGTH: 44
<212> TYPE: DNA
<213> ORGANISM: Artificial Sequence
<220> FEATURE:
<223> OTHER INFORMATION: synthetic

<400> SEQUENCE: 46
acacttgccg taacgtatct cctcatgttc atcgccgcgg acat        44

<210> SEQ ID NO 47
<211> LENGTH: 44
<212> TYPE: DNA
<213> ORGANISM: Artificial Sequence
<220> FEATURE:
<223> OTHER INFORMATION: synthetic

<400> SEQUENCE: 47
acgctagttg tcacgtatct cctcctgttc agccttacgg gaat        44

<210> SEQ ID NO 48
<211> LENGTH: 44
<212> TYPE: DNA
<213> ORGANISM: Artificial Sequence
<220> FEATURE:
<223> OTHER INFORMATION: synthetic

<400> SEQUENCE: 48
aagccggcaa tctcgtatct cctcttgttc caagcttacg ccca        44

<210> SEQ ID NO 49
<211> LENGTH: 44
<212> TYPE: DNA
<213> ORGANISM: Artificial Sequence
<220> FEATURE:
<223> OTHER INFORMATION: synthetic

<400> SEQUENCE: 49
attcttaccc tccctatctc ctcctgttct agtgccgctt acgt        44

<210> SEQ ID NO 50
<211> LENGTH: 44
<212> TYPE: DNA
<213> ORGANISM: Artificial Sequence
<220> FEATURE:
<223> OTHER INFORMATION: synthetic

<400> SEQUENCE: 50
accctgacct tcccgatctc ctcctgttca gtgacgagta cgta                        44

<210> SEQ ID NO 51
<211> LENGTH: 44
<212> TYPE: DNA
<213> ORGANISM: Artificial Sequence
<220> FEATURE:
<223> OTHER INFORMATION: synthetic

<400> SEQUENCE: 51
agttttaccg tcccgatctc ctcctgttcg gtgccgctta cgta                        44

<210> SEQ ID NO 52
<211> LENGTH: 43
<212> TYPE: DNA
<213> ORGANISM: Artificial Sequence
<220> FEATURE:
<223> OTHER INFORMATION: synthetic

<400> SEQUENCE: 52
aatataccgt aggtgatctc caacctgttc tgtgccgctt acc                         43

<210> SEQ ID NO 53
<211> LENGTH: 44
<212> TYPE: DNA
<213> ORGANISM: Artificial Sequence
<220> FEATURE:
<223> OTHER INFORMATION: synthetic

<400> SEQUENCE: 53
actccttacc gcccgtatct cctcctgttc cagtgccact tagt                        44

<210> SEQ ID NO 54
<211> LENGTH: 44
<212> TYPE: DNA
<213> ORGANISM: Artificial Sequence
<220> FEATURE:
<223> OTHER INFORMATION: synthetic

<400> SEQUENCE: 54
aatggatacg ttacgtatct cctcctgttc agtgcggcct tagt                        44

<210> SEQ ID NO 55
<211> LENGTH: 45
<212> TYPE: DNA
<213> ORGANISM: Artificial Sequence
<220> FEATURE:
<223> OTHER INFORMATION: synthetic

<400> SEQUENCE: 55
ggacctacgg ttcagtatct cctcctgttc ggttgccgct tacgt                       45

<210> SEQ ID NO 56
<211> LENGTH: 45
<212> TYPE: DNA
<213> ORGANISM: Artificial Sequence
<220> FEATURE:
<223> OTHER INFORMATION: synthetic

<400> SEQUENCE: 56
cgacctacgg ttcagtccgt agcgcaaatt cagtgttcgg cttcg                       45

<210> SEQ ID NO 57

<211> LENGTH: 44
<212> TYPE: DNA
<213> ORGANISM: Artificial Sequence
<220> FEATURE:
<223> OTHER INFORMATION: synthetic

<400> SEQUENCE: 57
cggattggcc tcagtccgta gcgcaaatag tgacgcttac tagg                 44

<210> SEQ ID NO 58
<211> LENGTH: 45
<212> TYPE: DNA
<213> ORGANISM: Artificial Sequence
<220> FEATURE:
<223> OTHER INFORMATION: synthetic

<400> SEQUENCE: 58
ataattaccg gtacagtccg tagcgcaaat caccggccgc ttacg                45

<210> SEQ ID NO 59
<211> LENGTH: 43
<212> TYPE: DNA
<213> ORGANISM: Artificial Sequence
<220> FEATURE:
<223> OTHER INFORMATION: synthetic

<400> SEQUENCE: 59
acacttgcag taacgtccgt agcgcaaatc agtgaagcgg aca                  43

<210> SEQ ID NO 60
<211> LENGTH: 44
<212> TYPE: DNA
<213> ORGANISM: Artificial Sequence
<220> FEATURE:
<223> OTHER INFORMATION: synthetic

<400> SEQUENCE: 60
aagcttattg tcacgtccgt agcgcaaatt ggttaatacg gatt                 44

<210> SEQ ID NO 61
<211> LENGTH: 46
<212> TYPE: DNA
<213> ORGANISM: Artificial Sequence
<220> FEATURE:
<223> OTHER INFORMATION: synthetic

<400> SEQUENCE: 61
cgacctacgg ttcagtccgt agcgcaaatt cagtgttcgg cttcgt               46

<210> SEQ ID NO 62
<211> LENGTH: 14
<212> TYPE: DNA
<213> ORGANISM: Artificial Sequence
<220> FEATURE:
<223> OTHER INFORMATION: synthetic

<400> SEQUENCE: 62 atctcctcctgttc                                                   14

<210> SEQ ID NO 63
<211> LENGTH: 14
<212> TYPE: DNA
<213> ORGANISM: Artificial Sequence
<220> FEATURE:
<223> OTHER INFORMATION: synthetic

<400> SEQUENCE: 63 atctgctcctgttc                                                      14

<210> SEQ ID NO 64
<211> LENGTH: 14
<212> TYPE: DNA
<213> ORGANISM: Artificial Sequence
<220> FEATURE:
<223> OTHER INFORMATION: synthetic

<400> SEQUENCE: 64 atctcctcatgttc                                                      14

<210> SEQ ID NO 65
<211> LENGTH: 14
<212> TYPE: DNA
<213> ORGANISM: Artificial Sequence
<220> FEATURE:
<223> OTHER INFORMATION: synthetic

<400> SEQUENCE: 65 atctcctcttgttc                                                      14

<210> SEQ ID NO 66
<211> LENGTH: 15
<212> TYPE: DNA
<213> ORGANISM: Artificial Sequence
<220> FEATURE:
<223> OTHER INFORMATION: synthetic

<400> SEQUENCE: 66 atctccaacctgttc                                                     15

<210> SEQ ID NO 67
<211> LENGTH: 13
<212> TYPE: DNA
<213> ORGANISM: Artificial Sequence
<220> FEATURE:
<223> OTHER INFORMATION: synthetic

<400> SEQUENCE: 67 ccgtagcgcaaat                                                       14

<210> SEQ ID NO 68
<211> LENGTH: 18
<212> TYPE: DNA
<213> ORGANISM: Artificial Sequence
<220> FEATURE:
<223> OTHER INFORMATION: synthetic

<400> SEQUENCE: 68 aattccgtaggtccagtg                                                  18

<210> SEQ ID NO 69
<211> LENGTH: 18
<212> TYPE: DNA
<213> ORGANISM: Artificial Sequence
<220> FEATURE:
<223> OTHER INFORMATION: synthetic

<400> SEQUENCE: 69 aattccgtcggtccagtg                                                  18

<210> SEQ ID NO 70
<211> LENGTH: 18
<212> TYPE: DNA

```
<213> ORGANISM: Artificial Sequence
<220> FEATURE:
<223> OTHER INFORMATION: synthetic

<400> SEQUENCE: 70 aattccgccggtccagtg                                              18

<210> SEQ ID NO 71
<211> LENGTH: 18
<212> TYPE: DNA
<213> ORGANISM: Artificial Sequence
<220> FEATURE:
<223> OTHER INFORMATION: synthetic

<400> SEQUENCE: 71 ggttccgagtctcgcgtg                                              18

<210> SEQ ID NO 72
<211> LENGTH: 18
<212> TYPE: DNA
<213> ORGANISM: Artificial Sequence
<220> FEATURE:
<223> OTHER INFORMATION: synthetic

<400> SEQUENCE: 72 cgttcaaaaggggcactg                                              18
```